United States Patent
Shameli et al.

(10) Patent No.: US 11,826,068 B2
(45) Date of Patent: Nov. 28, 2023

(54) METHOD OF FORMING SUCTION INSTRUMENT END AND SHAVER INSTRUMENT END

(71) Applicant: Acclarent, Inc., Irvine, CA (US)

(72) Inventors: Ehsan Shameli, Irvine, CA (US); Fatemeh Akbarian, Rancho Palos Verdes, CA (US); Todd A. Veloni, Orange, CA (US); Babak Ebrahimi, Irvine, CA (US)

(73) Assignee: Acclarent, Inc., Irvine, CA (US)

( * ) Notice: Subject to any disclaimer, the term of this patent is extended or adjusted under 35 U.S.C. 154(b) by 880 days.

(21) Appl. No.: 16/665,137

(22) Filed: Oct. 28, 2019

(65) Prior Publication Data

US 2020/0178996 A1    Jun. 11, 2020

Related U.S. Application Data

(60) Provisional application No. 62/777,302, filed on Dec. 10, 2018.

(51) Int. Cl.
*A61B 17/32* (2006.01)
*A61B 5/00* (2006.01)
(Continued)

(52) U.S. Cl.
CPC ...... *A61B 17/32002* (2013.01); *A61B 5/0055* (2013.01); *A61B 17/00234* (2013.01);
(Continued)

(58) Field of Classification Search
CPC ............... B23P 15/00; Y10T 29/49764; Y10T 29/4978; Y10T 29/49968;
(Continued)

(56) References Cited

U.S. PATENT DOCUMENTS 3,605,750 A * 9/1971 Sheridan et al. . A61M 25/0108
138/155
4,050,461 A * 9/1977 Ruby ...................... A61F 5/442
604/277
(Continued)

FOREIGN PATENT DOCUMENTS

DE        102012005536 A1     9/2013
WO       WO 2001/021338 A1    3/2001
WO       WO-2018006046 A1 *   1/2018    ....... A61B 17/00234

OTHER PUBLICATIONS

International Search Report and Written Opinion dated Jun. 23, 2020 for International Application No. PCT/IB2019/060374, 19 pages.
(Continued)

*Primary Examiner* — Sarang Afzali
*Assistant Examiner* — Darrell C Ford
(74) *Attorney, Agent, or Firm* — Frost Brown Todd LLP

(57) ABSTRACT

A method is used to manufacture a surgical instrument including a first tube, and a second tube. The first tube extends from a proximal first end portion to a distal first end portion. The second tube extends from a proximal second end portion to a distal second end portion. The second tube is positioned coaxially within the first tube with the distal second end portion positioned adjacent to the distal first end portion. The second tube defines a lumen. The sensor is secured proximal to the distal second end portion of the second tube. A die is engaged against a distal first end portion of the first tube while first tube rotates about its own longitudinal axis; and the die is simultaneously moved relative to the distal first end portion of the first tube along a predetermined path to form a predetermined shape.

20 Claims, 8 Drawing Sheets

(51) Int. Cl.
*A61B 17/00* (2006.01)
*B23P 15/00* (2006.01)
*B21D 41/04* (2006.01)
*B21D 22/14* (2006.01)
*A61B 17/24* (2006.01)

(52) U.S. Cl.
CPC .............. *B23P 15/00* (2013.01); *A61B 17/24* (2013.01); *A61B 2017/320032* (2013.01); *B21D 22/14* (2013.01); *B21D 41/04* (2013.01); *Y10T 29/4978* (2015.01); *Y10T 29/49764* (2015.01); *Y10T 29/49968* (2015.01)

(58) Field of Classification Search
CPC ......... A61B 2017/00526; A61B 2017/320024; A61B 17/32; A61F 9/00736
See application file for complete search history.

(56) References Cited

U.S. PATENT DOCUMENTS

| | | | | |
|---|---|---|---|---|
| 4,586,927 A * | 5/1986 | Jensen | .................... | A61F 5/442 604/341 |
| 4,598,710 A | 7/1986 | Kleinberg et al. | | |
| 4,811,734 A * | 3/1989 | McGurk-Burleson | | A61F 9/00763 30/240 |
| 5,412,682 A * | 5/1995 | Laudenslager | ........... | H01S 3/03 372/83 |
| 5,469,853 A * | 11/1995 | Law | ........................ | A61B 8/445 600/463 |
| 5,665,101 A * | 9/1997 | Becker | .................. | A61M 1/842 606/167 |
| 5,676,012 A * | 10/1997 | Ceriale | ............ | A61B 17/32002 72/370.02 |
| 5,782,849 A * | 7/1998 | Miller | .............. | A61B 17/32002 606/159 |
| 5,810,202 A * | 9/1998 | Hoback | ............... | A61M 5/1486 604/141 |
| 6,018,860 A * | 2/2000 | Smith | ...................... | B21G 1/08 451/130 |
| 6,258,111 B1 * | 7/2001 | Ross | .................... | A61F 9/00763 606/171 |
| 6,514,249 B1 * | 2/2003 | Maguire | .................. | A61N 7/02 606/41 |
| 6,742,236 B1 * | 6/2004 | Dion | ................ | A61B 17/32002 606/171 |
| 7,641,667 B2 * | 1/2010 | Sample | ............ | A61B 17/32002 407/53 |
| 7,720,521 B2 | 5/2010 | Chang et al. | | |
| 8,313,501 B2 * | 11/2012 | Miller | .................... | A61B 17/32 606/171 |
| 9,737,322 B2 * | 8/2017 | Oliver | .............. | A61B 17/32002 |
| 9,956,115 B2 * | 5/2018 | Rieger | ............. | A61B 17/32002 |
| 2002/0198492 A1 * | 12/2002 | Miller | ............... | A61M 25/1027 604/96.01 |
| 2004/0116957 A1 * | 6/2004 | Nishide | ............. | A61M 25/0054 604/528 |
| 2007/0093793 A1 * | 4/2007 | Maurer | .................. | B23K 11/02 606/4 |
| 2007/0123798 A1 * | 5/2007 | Rahamimov | ...... | A61B 1/00135 600/564 |
| 2008/0262410 A1 * | 10/2008 | Jenson | .................. | A61M 25/09 604/19 |
| 2009/0069831 A1 * | 3/2009 | Miller | .................... | A61B 17/32 606/171 |
| 2012/0190976 A1 * | 7/2012 | Kleinstreuer | .......... | A61B 34/70 604/247 |
| 2014/0364725 A1 | 12/2014 | Makower | | |
| 2016/0008083 A1 | 1/2016 | Kesten et al. | | |
| 2017/0296169 A1 * | 10/2017 | Yates | .................. | A61B 17/105 |
| 2018/0310886 A1 | 11/2018 | Salazar et al. | | |
| 2021/0401481 A1 * | 12/2021 | Croft | .................. | A61B 34/35 |

OTHER PUBLICATIONS

U.S. Appl. No. 62/741,594, entitled "Hollow Tube Surgical Instrument with Single Axis Sensor," filed Oct. 5, 2018.

* cited by examiner

METHOD OF FORMING SUCTION INSTRUMENT END AND SHAVER INSTRUMENT END

PRIORITY

This application claims priority to U.S. Provisional Pat. App. No. 62/777,302, entitled "Method of Forming Suction Instrument End and Shaver Instrument End," filed Dec. 10, 2018, the disclosure of which is incorporated by reference herein in its entirety.

BACKGROUND

Surgical instruments, such as surgical suction instruments and surgical cutting instruments, contain features that facilitate operation within or adjacent to an anatomical passageway of a patient, such as during incisions of muscosa, removal of bone, or dilation of an anatomical passageway. Anatomical passageways that may undergo such operations may include ostia of paranasal sinuses (e.g., to treat sinusitis), the larynx, the Eustachian tube, or other passageways within the ear, nose, or throat, etc. In addition to the above described operations, or similar operations, it may be desirable to apply suction and/or irrigation within or adjacent to an anatomical passageway before, during, or after the above described operations, or similar operations via a surgical suction instrument. One method of applying suction within or adjacent to an anatomical passageway of a patient involves obtaining the surgical suction instrument having an elongate shaft defining a lumen terminating at an open distal end of the elongated shaft such that the lumen is in fluid communication with an external suction source. An operator may then insert the distal end of the elongate shaft within the nostril or mouth of a patient toward a desired location within the patient. With the distal end of the elongate shaft inserted within the patient, an operator may manipulate the surgical suction instrument and/or suction source to remove extraneous and/or undesired matter near or within an anatomical passageway of a patient. Applying suction and/or irrigation during an operation may be beneficial for multiple purposes as will be apparent to those skilled in the art.

Surgical cutting instruments may also include suction features and are configured for removal of lesions, polyps and fibroids within the nasal cavity are known. Some configurations may include an elongated inner member rotatably coaxially disposed within a tubular outer member. The distal end of the outer member includes an opening, and the distal end of the inner member includes cutting edges. The proximal ends of the two members may be connected to a handle directly or via a detachable hub. The inner member may be hollow and in communication with an aspiration port so that severed tissue, etc. can be aspirated out through the hollow member. The cutting edges can have any various configurations suitable for the particular type of tissue, such as bone tissue, to be done, with the opening configured to cooperate with the specific cutting edge configuration.

Both surgical suction and cutting instruments may be located within the patient in some instances with cooperative use of an image-guided surgery (IGS) system. IGS is a technique where a computer is used to obtain a real time correlation of the location of an instrument that has been inserted into a patient's body to a set of preoperatively obtained images (e.g., a CT or MRI scan, 3-D map, etc.) so as to superimpose the current location of the instrument on the preoperatively obtained images. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) mounted thereon are used to perform the procedure while the sensors send data to the computer indicating the current position of each surgical instrument. The computer correlates the data it receives from the instrument-mounted sensors with the digital map that was created from the preoperative tomographic scan. The tomographic scan images are displayed on a video monitor along with an indicator (e.g., cross hairs or an illuminated dot, etc.) showing the real time position of each surgical instrument relative to the anatomical structures shown in the scan images. In this manner, the surgeon is able to know the precise position of each sensor-equipped instrument by viewing the video monitor even if the surgeon is unable to directly visualize the instrument itself at its current location within the body.

When applied to functional endoscopic sinus surgery (FESS), balloon sinuplasty, and/or other ENT procedures, the use of IGS systems allows the surgeon to achieve more precise movement and positioning of the surgical instruments than can be achieved by viewing through an endoscope alone. This is so because a typical endoscopic image is a spatially limited, 2-dimensional, line-of-sight view. The use of IGS systems provides a real time, 3-dimensional view of all of the anatomy surrounding the operative field, not just that which is actually visible in the spatially limited, 2-dimensional, direct line-of-sight endoscopic view. As a result, IGS may be particularly useful during performance of FESS, balloon sinuplasty, and/or other ENT procedures where normal anatomical landmarks are not present or are difficult to visualize endoscopically.

It may be desirable to efficiently manufacture surgical instruments that contain sensors for use with navigation systems, such as IGS systems. While several different methods to manufacture surgical instruments configured for suction, cutting, and/or removal of tissue from within the body, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
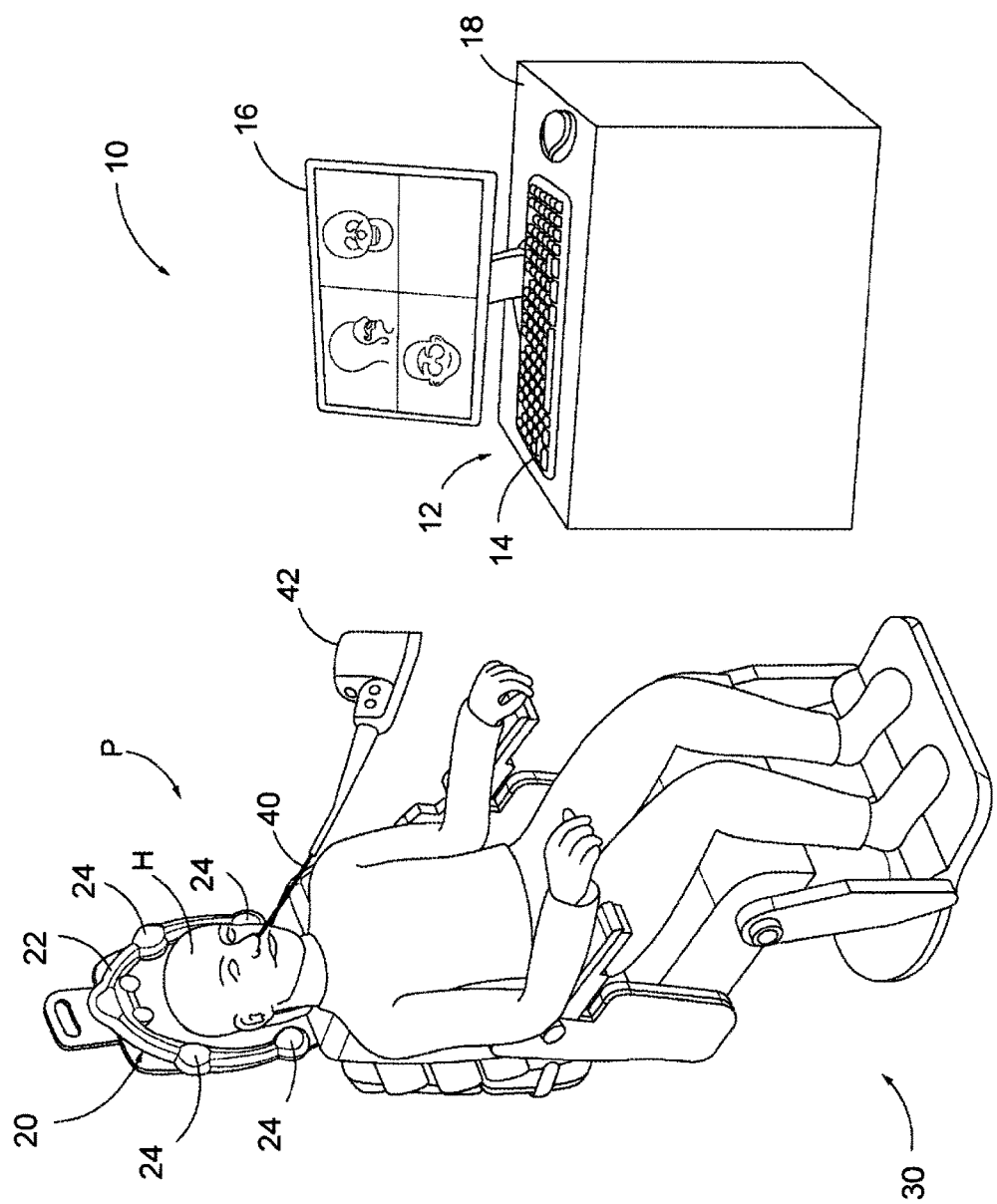
FIG. 1 depicts a schematic view of an exemplary surgery navigation system being used on a patient seated in an exemplary medical procedure chair.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "clockwise", "counterclockwise". "axial," and "longitudinal" also are used herein for reference to relative positions and directions. Rotation is clockwise when viewed from the proximal end. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. IMAGE GUIDED SURGERY NAVIGATION SYSTEM

FIG. 1 shows an exemplary IGS navigation system (10) enabling an ENT procedure to be performed using image guidance. When performing a medical procedure within a head (H) of a patient (P), it may be desirable to have information regarding the position of an instrument within the head (H) of the patient (P), particularly when the instrument is in a location where it is difficult or impossible to obtain an endoscopic view of a working element of the instrument within the head (H) of the patient (P). In addition to or in lieu of having the components and operability described herein IGS navigation system (10) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein; and U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein.

IGS navigation system (10) of the present example comprises a field generator assembly (20), which comprises set of magnetic field generators (24) that are integrated into a horseshoe-shaped frame (22). Field generators (24) are operable to generate alternating magnetic fields of different frequencies around the head (H) of the patient (P). A navigation guidewire (40) is inserted into the head (H) of the patient (P) in this example. Navigation guidewire (40) may be a standalone device or may be positioned on an end effector or other location of a medical instrument such as a surgical cutting instrument or dilation instrument. In the present example, frame (22) is mounted to a chair (30), with the patient (P) being seated in the chair (30) such that frame (22) is located adjacent to the head (H) of the patient (P). By way of example only, chair (30) and/or field generator assembly (20) may be configured and operable in accordance with at least some of the teachings of U.S. Pub. No. 2018/0310886, entitled "Apparatus to Secure Field Generating Device to Chair," published Nov. 1, 2018, issued as U.S. Pat. No. 10,561,370 on Feb. 18, 2020,the disclosure of which is incorporated by reference herein.

IGS navigation system (10) of the present example further comprises a processor (12), which controls field generators (24) and other elements of IGS navigation system (10). For instance, processor (12) is operable to drive field generators (24) to generate alternating electromagnetic fields; and process signals from navigation guidewire (40) to determine the location of a sensor in navigation guidewire (40) within the head (H) of the patient (P). Processor (12) comprises a processing unit communicating with one or more memories. Processor (12) of the present example is mounted in a console (18), which comprises operating controls (14) that include a keypad and/or a pointing device such as a mouse or trackball. A physician uses operating controls (14) to interact with processor (12) while performing the surgical procedure.

Navigation guidewire (40) includes a sensor (not shown) that is responsive to positioning within the alternating magnetic fields generated by field generators (24). A coupling unit (42) is secured to the proximal end of navigation guidewire (40) and is configured to provide communication of data and other signals between console (18) and navigation guidewire (40). Coupling unit (42) may provide wired or wireless communication of data and other signals.

In the present example, the sensor of navigation guidewire (40) comprises at least one coil at the distal end of navigation guidewire (40). When such a coil is positioned within an alternating electromagnetic field generated by field generators (24), the alternating magnetic field may generate electrical current in the coil, and this electrical current may be communicated along the electrical conduit(s) in navigation guidewire (40) and further to processor (12) via coupling unit (42). This phenomenon may enable IGS navigation system (10) to determine the location of the distal end of navigation guidewire (40) or other medical instrument (e.g., dilation instrument, surgical cutting instrument, etc.) within a three-dimensional space (i.e., within the head (H) of the patient (P), etc.). To accomplish this, processor (12) executes an algorithm to calculate location coordinates of the distal end of navigation guidewire (40) from the position related signals of the coil(s) in navigation guidewire (40). While the sensor is located in navigation guidewire (40) in this example, such a position sensor may be integrated into various other kinds of instruments, including those described in greater detail below.

Processor (12) uses software stored in a memory of processor (12) to calibrate and operate IGS navigation system (10). Such operation includes driving field generators (24), processing data from navigation guidewire (40), processing data from operating controls (14), and driving display screen (16). In some implementations, operation may also include monitoring and enforcement of one or more safety features or functions of IGS navigation system (10). Processor (12) is further operable to provide video in real time via display screen (16), showing the position of the distal end of navigation guidewire (40) in relation to a video camera image of the patient's head (H), a CT scan image of the patient's head (H), and/or a computer-generated three-dimensional model of the anatomy within and adjacent to the patient's nasal cavity. Display screen (16) may display such images simultaneously and/or superimposed on each other during the surgical procedure. Such displayed images may also include graphical representations of instruments that are inserted in the patient's head (H), such as navigation guidewire (40), such that the operator may view the virtual rendering of the instrument at its actual location in real time. By way of example only, display screen (16) may provide images in accordance with at least some of the teachings of U.S. Pat. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein. In the event that the operator is also using an endoscope, the endoscopic image may also be provided on display screen (16).

The images provided through display screen (16) may help guide the operator in maneuvering and otherwise manipulating instruments within the patient's head (H) when such instruments incorporate navigation guidewire (40). It should also be understood that other components of a surgical instrument and other kinds of surgical instruments, as described below, may incorporate a sensor like the sensor of navigation guidewire (40).

II. SURGICAL CUTTING INSTRUMENT

Figure 2:
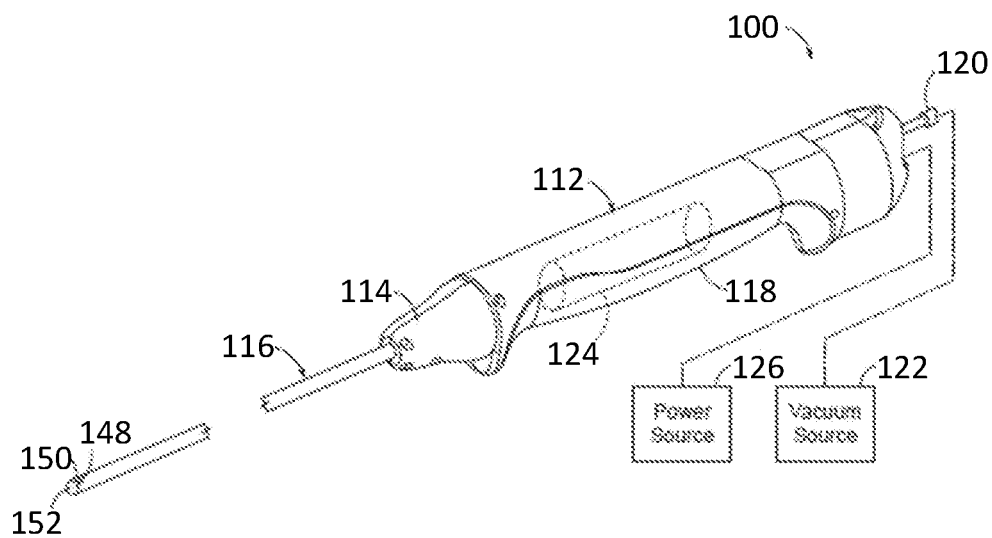
FIG. 2 depicts a perspective view of an exemplary surgical cutting instrument having a handle assembly and a cutter shaft assembly.
Figure 3:
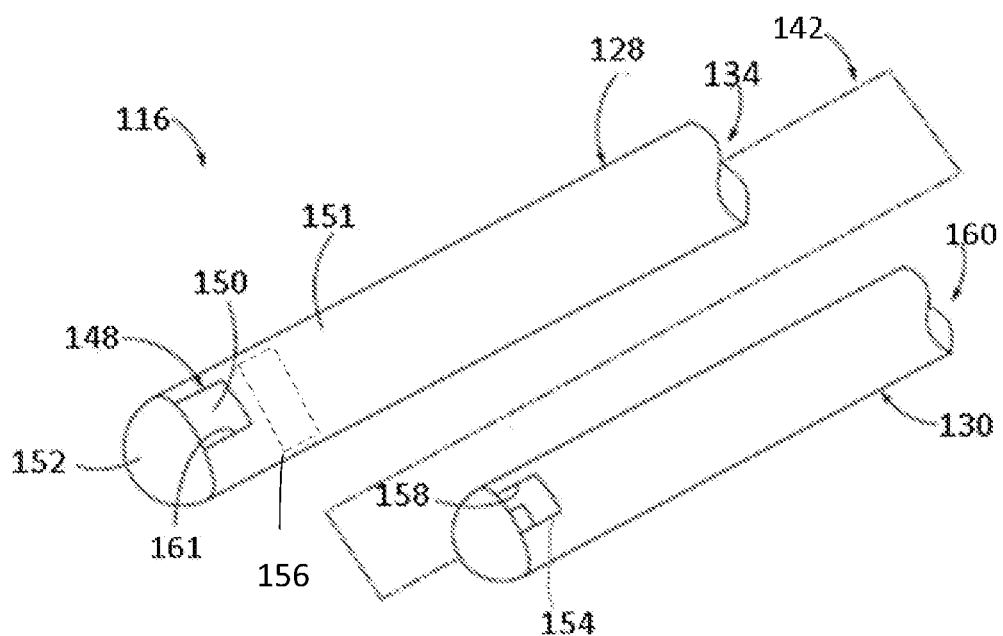
FIG. 3 depicts an enlarged, exploded perspective view of the cutter shaft assembly of FIG. 2 having an outer shaft after being end formed, a cutting member, and a sensor.

FIGS. 2-3 depict a surgical cutting instrument (100) that may be used to remove tissue, such as bone tissue, from the nasal cavity, as well as from any other suitable location. Surgical cutting instrument (100) of the present example includes a handle assembly (112), a hub (114), and an example of a cutter shaft assembly (116) extending distally from handle assembly (112). Handle assembly (112) has a handle (118) which may be of any suitable configuration. Handle (118) may include controls for the operation of surgical cutting instrument (100), or the controls may be located remotely. Surgical cutting instrument (100) further includes a suction port (120) operatively connected to a vacuum source (122) and configured to enable aspiration of tissue, such as a bone tissue, from a surgical site. Rotational motion is delivered by a motorized drive assembly (124) within handle assembly (112) to cutter shaft assembly (116) in the present example, although any suitable rotational or oscillatory motion source may be utilized. For example, such motion source may be housed within handle assembly (112) or may be external and connectable to handle assembly (112). A power source (126) connects to motorized drive assembly (124) to power surgical cutting instrument (100) for use. In addition or alternatively, handle assembly (112) may house a battery (not shown).

A. Cutter Shaft Assembly

Cutter shaft assembly (116) generally includes an outer shaft (128) and an inner cutting member (130), which may also be referred to herein as an inner cutting shaft (130), collectively configured to receive and remove tissue from the surgical site. Inner cutting member (130), which is illustrated as a tube, is disposed within a longitudinally extending lumen (134) of outer shaft (128), which is also illustrated as another tube. Inner cutting member (130) is configured to be rotated about a longitudinal axis (142) of cutter shaft assembly (116). Although cutter shaft assembly (116) is depicted as rigid, all or a portion of cutter shaft assembly (116) may be flexible, with longitudinal axis (142) comprising a series of cross-sectional centers. Inner cutting member (130) defines an lumen (160) and extends proximally to handle assembly (112) and connects to motorized drive assembly (124), which rotatably drives inner cutting member (130) relative to outer shaft (128). While the present examples of outer shaft (128) and inner cutting member (130) are hollow tubes, it will be appreciated that outer shaft (128) and inner cutting member (130) may take alternative elongate shapes sized for accessing an anatomical passageway and may either respectively define lumens (134, 160) or having alternative lumen structures extending therethrough. Outer shaft (128) and inner cutting member (130) are not intended to be unnecessarily limited to being hollow tubes.

Outer shaft (128) includes a window region (148) having a shaft opening, such as a shaft window opening (150), at a distal portion of outer shaft (128). Outer shaft (128) includes a tubular sidewall (151) that distally terminates in a curved end, such as a generally hemi-spherical end (152). Shaft window opening (150) extends through tubular sidewall (151) of outer shaft (128) into lumen (134). Shaft window opening (150) faces radially outward relative to longitudinal axis (142) such that tissue is configured to be radially received through shaft window opening (150) into a centrally located lumen (160) of inner cutting member (130) in a radially inward direction. Shaft window opening (150) is surrounded by a relatively dull edge (161).

Inner cutting member (130) includes a cutting window opening (154) at a distal portion of inner cutting member (130). Cutting window opening (154) is configured to longitudinally align with shaft window opening (150) and includes a cutting edge (158) extending therealong. It is noted that less than the entirety of cutting edge (158) may be configured for cutting tissue against an opposing dull edge (161) of outer shaft (128). At least a portion of cutting edge (158) is disposed to move adjacent to and across at least a portion of window region (148) when inner cutting member (130) is rotated or oscillated about longitudinal axis (142). By way of example, as inner cutting member (130) moves in a clockwise direction, dull edge (161) of window region (148) provides an opposing surface to cutting edge (158) whereby tissue may be severed to remove a cut tissue portion therefrom. Cutting edge (158) and dull edge (161) may have any configuration which suitably cooperates with the other to sever tissue, such as a knife edge, a serrated edge, bipolar, monopolar or harmonic energy modality, or laser activated cutting edge.

The extent of movement and position of cutting edge (158) relative to dull edge (161) is sufficient to separate tissue, whether by severing, tearing or any other mechanism. For example, cutting edge (158) may cyclically move across at least a portion of window region (148). Further clockwise movement of inner cutting member (130) will advance cutting edge (158) past dull edge (161), such as results from oscillation about longitudinal axis (142) or from full rotation about longitudinal axis (142).

Furthermore, surgical cutting instrument (100) may be used in conjunction with an image-guide surgery (IGS) navigation system (10) as described above. In particular, the distal end of outer shaft (128) may include a position sensor (156) like the position sensor (not shown) of navigation guidewire (40) described above. By way of example only, outer shaft (128) may incorporate one or more position sensors in accordance with at least some of the teachings of U.S. Pat. App. No. 62/741,594, entitled "Hollow Tube Surgical Instrument with Single Axis Sensor," filed Oct. 5, 2018, the disclosure of which is incorporated by reference herein. Like the above-described position sensor of navigation guidewire (40), position sensor (156) of surgical cutting instrument (100) may be configured to generate signals in response to an alternating electromagnetic field generated by field generators (24); and those generated signals may be indicative of the position of position sensor (156) within the three-dimensional space of the electromagnetic field. This position information may further indicate the position of the distal end of outer shaft (128) within the head (H) of the patient (P), such that IGS navigation system (10) may drive display screen (16) to indicate the position of the distal end of outer shaft (128) on preoperatively obtained images (e.g., CT scan images) of the head (H) of the patient (P). Some other versions of surgical cutting instrument (100) may omit position sensor (156), as position sensor (156) is merely optional.

B. End Formed Manufacturing of the Cutter Shaft Assembly

Surgical cutting instrument (100), may be manufactured with outer shaft (128) and/or inner cutting member (130) each formed from a plurality of components assembled together, such as by welding a distal cap on a proximal tube. While attaching multiple components together to manufacture either one or both of outer shaft (128) or inner cutting member (130) may be beneficial in some instances, such attachments may be inadvertently formed weak, misshapen, or even damage surrounding materials or features. In contrast, end forming is a manufacturing process that may be used to form an end of an elongate member, such as outer shaft (128) and/or inner cutting member (130), into predetermined shape while reducing components and associated attachments therebetween.

Figure 4:
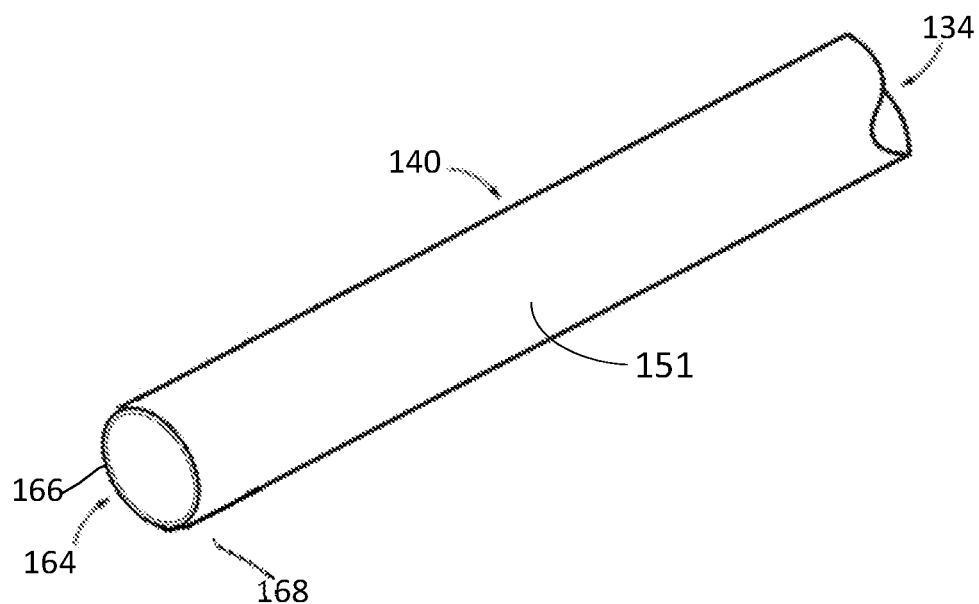
FIG. 4 depicts an enlarged perspective view of the outer shaft similar to FIG. 3, but having a tubular distal end that is in a state before being end formed.

While FIGS. 2-3 show fully-manufactured surgical cutting instrument (100), FIG. 4 shows outer stock shaft (140) before being end formed into outer shaft (128). Tubular sidewall (151) extends from proximal end (not shown) to a distal end (164). Tubular sidewall (151) of outer stock shaft (140) has a uniform shape from proximal end (not shown) to distal end (164). Distal end (164) more particularly distally terminates at distal end annular edge (166), such that outer stock shaft (140) is in the form of a simple hollow tube with lumen (134) that is fully open at each terminal end of outer stock shaft (140).

Figure 5:
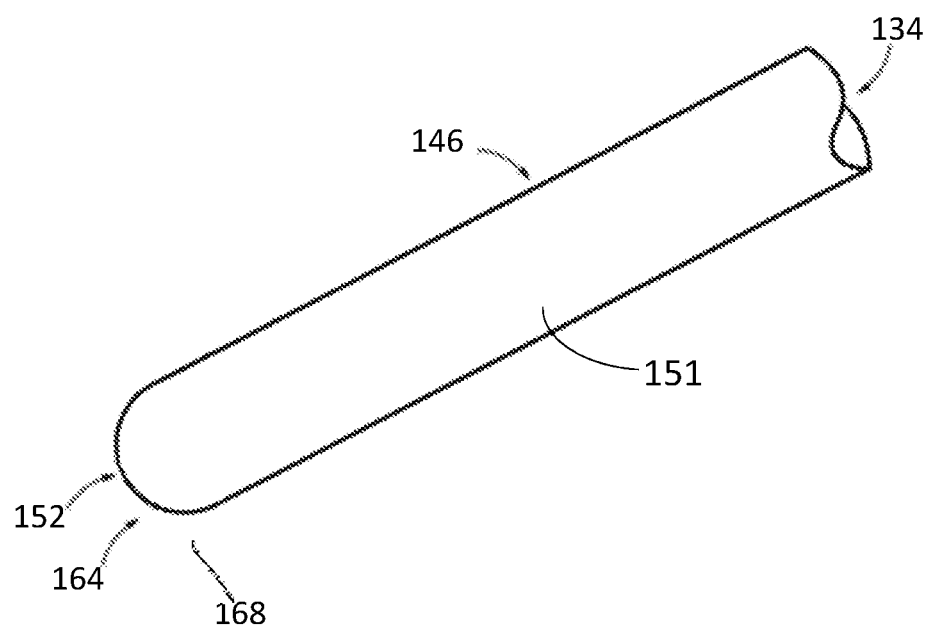
FIG. 5 depicts an enlarged perspective view of the outer shaft similar to FIG. 4, but having a hemi-spherically dome shaped distal end after being end formed.
Figure 6:
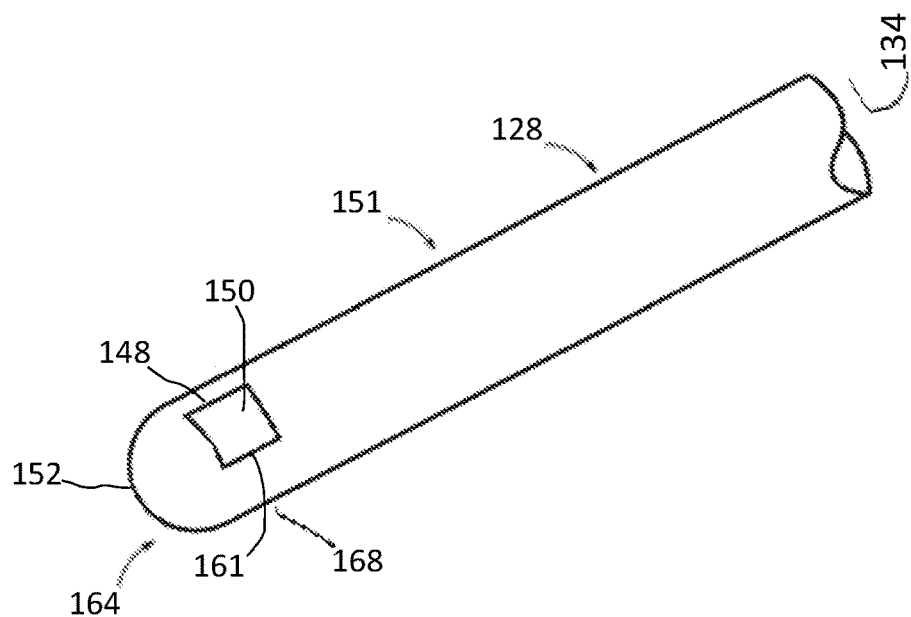
FIG. 6 depicts an enlarged view of the outer shaft similar to FIG. 5, but having a shaft window opening formed therein after being end formed.

With respect to FIGS. 4-5, end forming generally includes a die configured to shape distal end annular edge (166) to a predetermined shape. To this end, outer stock shaft (140) is rotatably driven about the central longitudinal axis of outer stock shaft (140), such as by a lathe, while the die engages distal end (164) of outer stock shaft (140). The die may include a hemispherical recess into which distal end (164) is engaged. The die continues to be urged against distal end annular edge (166) while moving relative to outer stock shaft (140) along a predetermined path to form distal end (164) into the predetermined shape, such as hemi-spherical end (152) of the present example. By way of example only, the die may rock orbitally, arcuately, or in any other fashion around distal end (164) of outer stock shaft (140) while outer stock shaft (140) is rotated at high speed about the central longitudinal axis of outer stock shaft (140). Frictional engagement between the die and distal end (164) further generates heat to aid in the end forming process, although, in some instances, additional heat may be added to more effectively form distal end (164) of outer stock shaft (140).

End forming continues until hemi-spherical end (152) encapsulates lumen (134) at distal end (164) as shown in FIG. 5, thereby forming outer stock shaft (140) into outer formed shaft (146). A weld may be added to seal hemi-spherical end (152) in some examples. While the present example shows hemi-spherical end (152), it will be appreciated that alternative shapes may similarly be formed by end forming such that the invention is not intended to be unnecessarily limited to hemi-spherical end (152) shown in FIG. 5.

Figure 7:
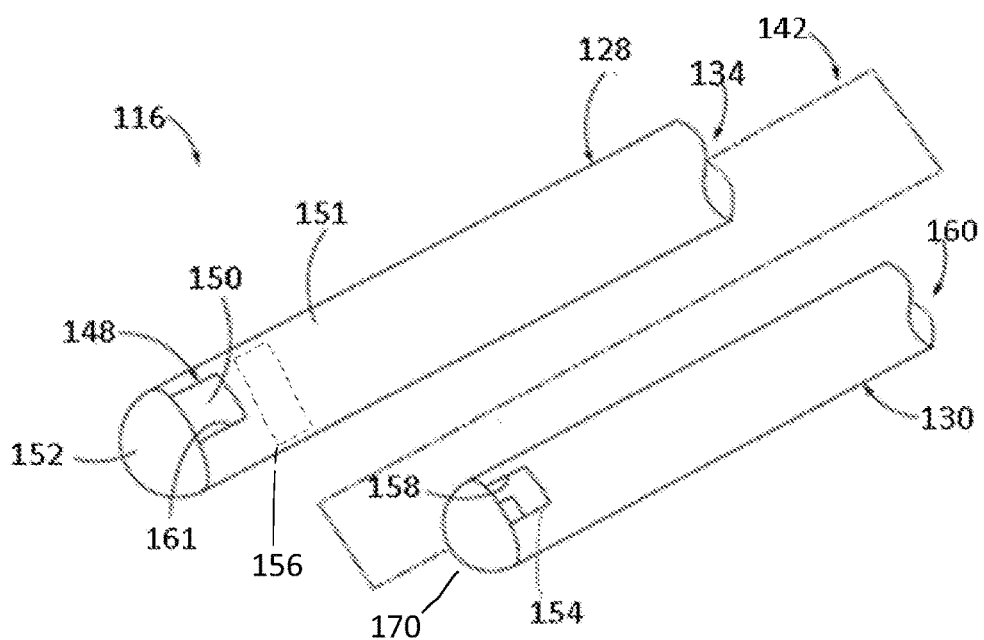
FIG. 7 depicts an enlarged, exploded perspective view the outer shaft of FIG. 6 receiving the cutting member of FIG. 3 during assembly.

Once hemi-spherical end (152) is formed with outer formed shaft (146), shaft window opening (150) is machined through tubular sidewall (151) at distal end portion (168) of outer formed shaft (146). Shaft window opening (150) extends through tubular sidewall (151) into lumen (134) and faces radially outward relative to longitudinal axis (142) (see FIG. 7). A relatively dull edge (161) surrounds shaft window opening (150), but further machining may occur on dull edge (161) to remove any remaining burrs from formation of shaft window opening (150). Outer formed shaft (146) is thereby manufactured into outer shaft (128) for further assembly as shown in FIG. 7. While outer shaft (128) is end formed as discussed above, inner cutting member (130) may be similarly end formed. The invention is thus not intended to be unnecessarily limited to only end forming outer shaft (128).

FIG. 7 shows inner cutting member (130) being coaxially inserted into outer shaft (128) for assembly. More particularly, a distal end (170) of inner cutting member (130) is distally inserted into proximal end (not shown) of lumen (134). Once inserted therein, inner cutting member (130) distally translates through outer shaft (128) until distal end (170) of inner cutting member (130) is proximate to distal end (164) of outer shaft (128). Cutting window opening (154) is longitudinally aligned along longitudinal axis (142) at distal end portion (168) with shaft window opening (150)

so that cutting window opening (154) is in fluid communication with shaft window opening (150) to complete assembly of cutter shaft assembly (116). Cutter shaft assembly (116) may then be attached to handle assembly (112) (see FIG. 2) to complete manufacture of surgical cutting instrument (100) for use.

III. SURGICAL SUCTION INSTRUMENT

Figure 8:
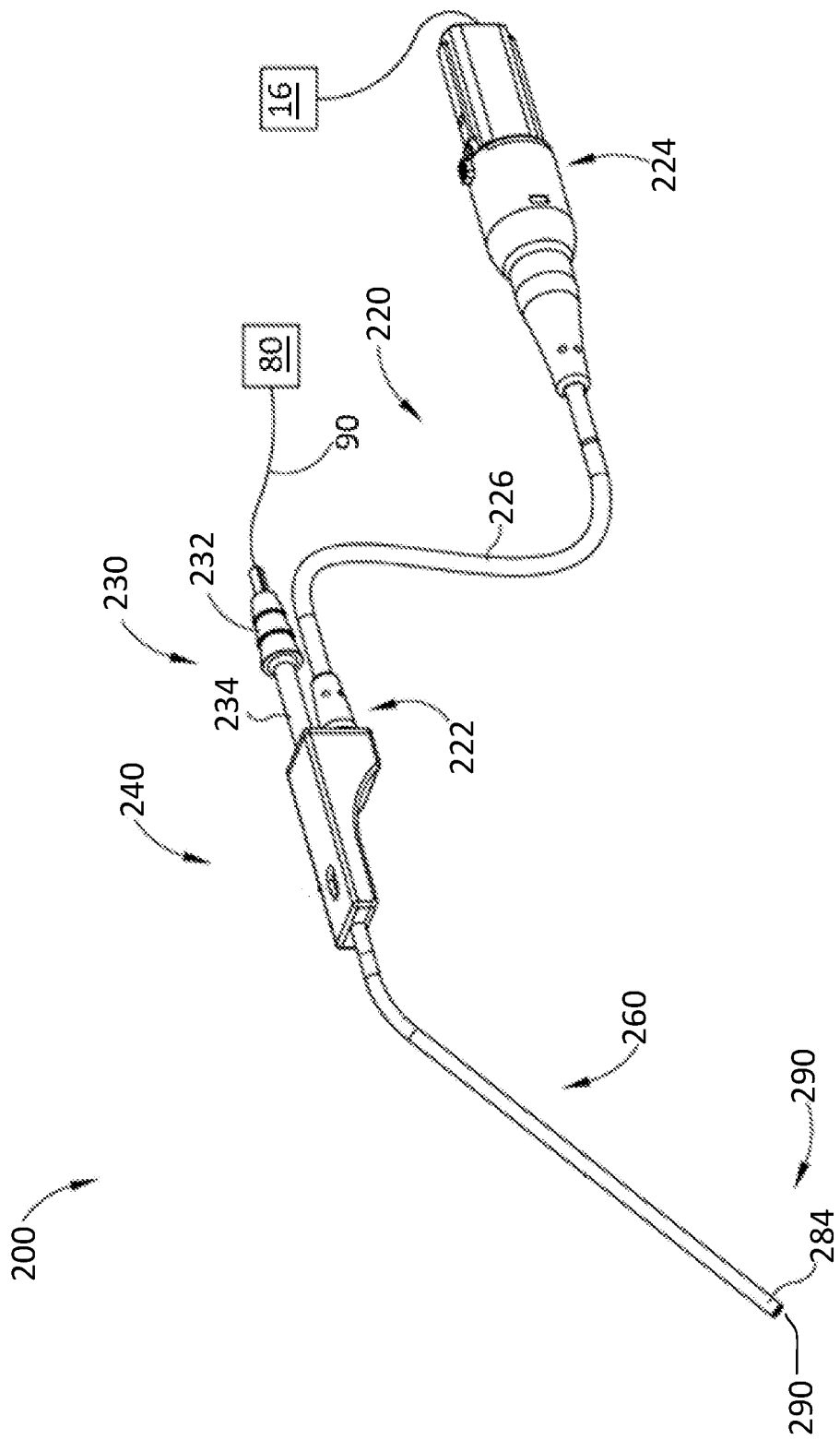
FIG. 8 depicts a perspective view of an exemplary surgical suction instrument having a suction shaft assembly with an outer shaft and an inner shaft.

FIG. 8 shows a surgical suction instrument (200) that may be used to remove tissue, fluid, and/or debris from anatomical passageways located in the body. Surgical suction instrument (200) is configured for use in conjunction with IGS navigation system (10) (see FIG. 1). Surgical suction instrument (200) is fluidly coupled with suction source (80). Suction source (80) may comprise a vacuum pump and a fluid reservoir, among other components, as is known in the art. Suction source (80) is configured to provide enough suction to pull excess fluid and/or debris through surgical suction instrument (200). Surgical suction instrument (200) is in communication with IGS navigation system (10) (see FIG. 1) via console (18). Surgical suction instrument (200) is configured to communicate with console (18) such that processor (12) (see FIG. 1) may execute an algorithm to calculate location coordinates of a selected portion of surgical suction instrument (200). Therefore, surgical suction instrument (200) is in communication with IGS navigation system (10) (see FIG. 1) such that IGS navigation system (10) (see FIG. 1) may calculate, track, and display the spatial location of a portion of surgical suction instrument (200) relative to a three-dimensional model of the anatomy within or adjacent to a patient's nasal cavity.

Surgical suction instrument (200) includes a coupling unit (220), a proximal suction conduit port (230), a grip portion (240), and an elongate cannula assembly (260). A distal end (290) of elongate cannula assembly (260) may be inserted, transnasally or otherwise, within or adjacent to a nasal cavity of a patient (or elsewhere within a patient) to provide suction. As will be described in greater detail below, elongate cannula assembly (260) includes a sensor (256) (see FIG. 10) that may communicate data corresponding to the 3-dimensional spatial position of elongate cannula assembly (260) to console (18) via coupling unit (220). Sensor (256) is thus similar to position sensor (156) of surgical cutting instrument (100) and the sensor of navigation guidewire (40) as described above.

Coupling unit (220) includes a sensor coupling (222), a console coupling (224), and a cable (226) connecting and establishing communication between sensor coupling (222) and console coupling (224). Sensor coupling (222) includes prongs (not shown) that are housed within a proximal cavity (not shown) of grip portion (240). Console coupling (224) is configured to couple with console (18) of surgical suction instrument (200) such that sensor (256) (see FIG. 10) is in communication with console (18). Console coupling (224) may be in wired or wireless communication with console (18). In some versions, coupling unit (220) simply communicates data or other signals from selected portion of surgical suction instrument (200) to console (18) uni-directionally, without also communicating data or other signals from console (18). In some other versions, coupling unit (220) provides bidirectional communication of data or other signals between selected portions of surgical suction instrument (200) to console (18). Various other suitable features and functionality that may be incorporated into coupling unit (220) will be apparent to those of ordinary skill in the art in view of the teachings herein.

Proximal suction conduit port (230) includes a proximal barbed configuration (232) connected to a distal shaft (234) that extends into grip portion (240). Proximal suction conduit port (230) defines a pathway (not shown) that extends from an open end of proximal barbed configuration (232) to an open end of distal shaft (234). Proximal barbed configuration (232) is configured to provide a secure fit with conduit (90) such that pathway (not shown) and the interior of conduit (90) are in fluid communication with each other. While the present example uses proximal barbed configuration (232) to provide a secure fit with conduit (90), it should be understood that various other kinds of configurations may be used to provide a secure fit between proximal suction conduit port (230) and conduit (90). Pathway (not shown) is dimensioned to receive a portion of elongate cannula assembly (260) such that elongate cannula assembly (260) is in fluid communication with conduit (90), and therefore suction source (80).

A. Suction Shaft Assembly

Figure 9:
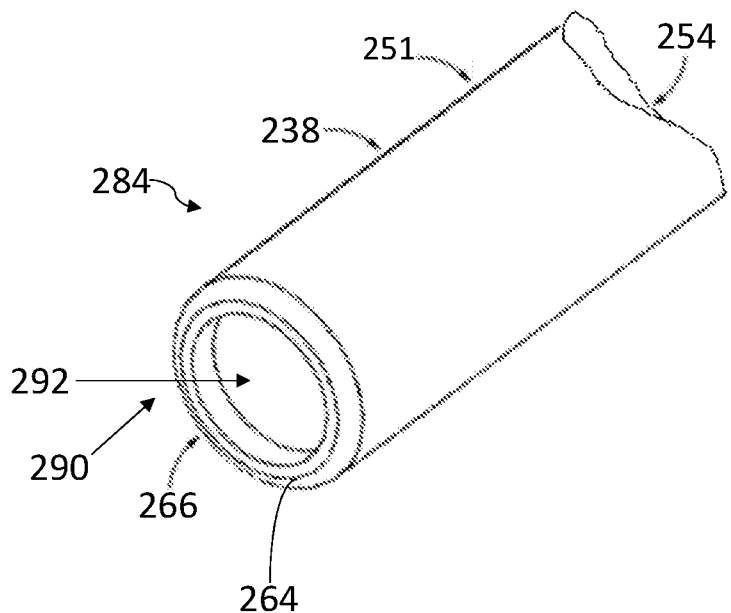
FIG. 9 depicts an enlarged perspective view of a distal end portion of the suction instrument of FIG. 8.
Figure 10:
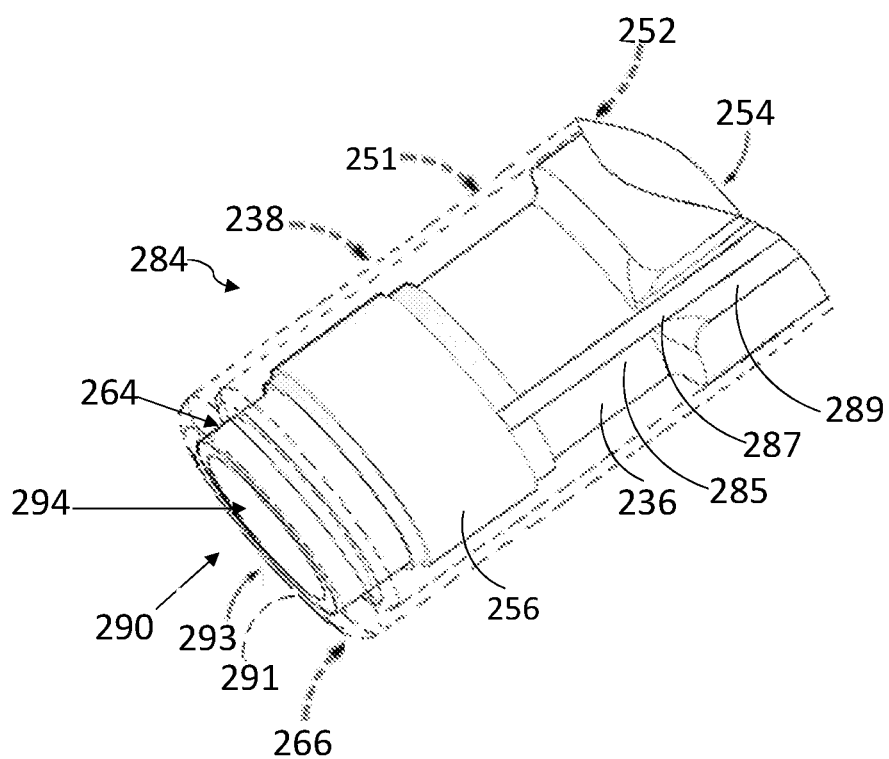
FIG. 10 depicts an enlarged perspective view of the distal end portion of the suction instrument of FIG. 9 having the outer shaft shown in phantom for greater clarity of a sensor positioned on the inner shaft.

Elongate cannula assembly (260), referred to hereunder as suction shaft assembly (260), generally includes an outer shaft (238), an inner shaft (236), and sensor (256) and is shown in FIGS. 9-10 in greater detail. Inner shaft (236), which is illustrated as a tube, is disposed within a longitudinally extending lumen (254) of outer shaft (238), which is also illustrated as another tube. Inner shaft (236) defines an inner lumen (254) and extends from an aperture (294) at distal end (290) toward grip portion (240) (see FIG. 8) and is fluidly coupled with suction source (80) (see FIG. 8).

Sensor (256) is mounted on inner shaft (236) at a distal end portion (284) and is in communication with console (18) (see FIG. 1). More particularly, sensor (256) is positioned on a necked down end portion (285) of inner shaft (236) with an electrical wire (287) proximally extending therefrom along an elongate channel (289). A fillet (266) is positioned on distal end (290) of outer shaft (238) to define an inner annular surface (291). Inner annular surface (291) defines a coaxial diameter sized to engage inner tube outer diameter (264) of inner shaft (236). Engagement between inner annular surface (291) of outer shaft (238) and necked down end portion (285) of inner shaft (236) secured and sealed together by a weld to define a sealed seam (293) therebetween for use in the patient.

B. End Formed Manufacturing of the Suction Shaft Assembly

Surgical suction instrument (200) may be manufactured with outer shaft (238) and/or inner shaft (236) each formed from a plurality of components assembled together, such as by welding a distal cap on a proximal tube. While attaching multiple components together to manufacture either one or both of outer shaft (238) or inner shaft (236) may be beneficial in some instances, such attachments may be inadvertently formed weak, misshapen, or even damage surrounding materials or features. By way of example, welding components together adjacent to sensor (256) may increase the likelihood of damaging sensor (256) during manufacture. In contrast, manufacturing outer shaft (238) by end forming may reduce the number of components and associated attachments therebetween to reduce the likelihood of sensor damage. Using an end forming process may further enhance robustness of the distal end of elongate cannula assembly (260) by reducing the risk of two coupled parts becoming decoupled from each other during a medical procedure.

Figure 11:
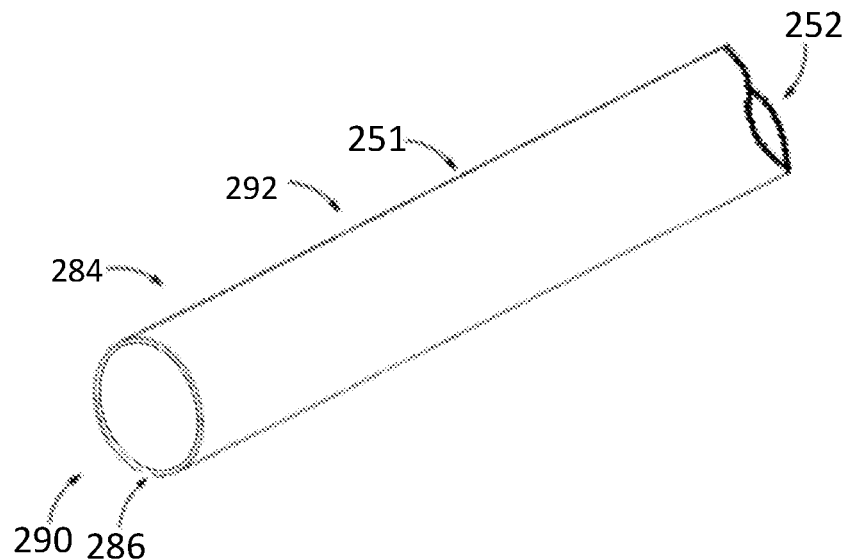
FIG. 11 depicts an enlarged perspective view of the outer shaft of FIG. 8 having a tubular distal end that is in a state before being end formed.

While FIGS. 8-10 show manufactured surgical suction instrument (200), FIG. 11 shows an outer stock shaft (292) before being end formed. Tubular sidewall (251) extends from proximal end (not shown) to a distal end (290) and has a uniform shape extending therealong. Distal end (290) of outer stock shaft (292) distally terminates at a distal end annular edge (286), such that outer stock shaft (292) is in the form of a simple hollow tube with outer lumen (252) that is fully open at each terminal end of outer stock shaft (292).

Figure 12:
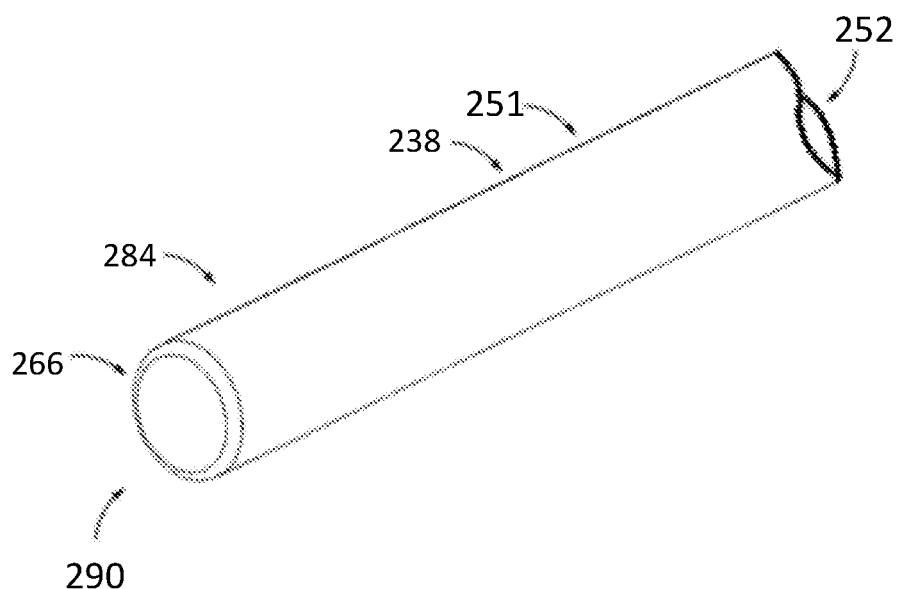
FIG. 12 depicts an enlarged perspective view of the outer shaft similar to FIG. 10, but having a surrounding annular fillet after being end formed.

With respect to FIGS. 11-12, end forming generally includes a die configured to shape distal end annular edge (286) to a predetermined shape. To this end, outer stock shaft (292) is rotatably driven about the central longitudinal axis of outer stock shaft (292), such as by a lathe, while the die engages distal end (290) of outer stock shaft (292). The die may include a hemispherical recess or other feature into which distal end (290) is engaged. The die continues to be urged against distal end annular edge (286) while moving relative to outer stock shaft (292) along a predetermined path to form distal end (290) into the predetermined shape, such as fillet (266) with inner annular surface (291). Dimensions of inner annular surface (291) may be tightly controlled during end forming to size inner annular surface (291) (see FIG. 13) to engage an inner tube outer diameter (264) (see FIG. 13) of necked down end portion (285) (see FIG. 13). Frictional engagement between the die and distal end (290) further generates heat to aid in the end forming process, although, in some instances, additional heat may be added to more effectively form distal end (290) of the outer stock shaft (292).

End forming continues until fillet (266) with inner annular surface (291) is formed to completely surround lumen (254) as outer shaft (238) in FIG. 12 for assembly. While the present example shows fillet (266), it will be appreciated that alternative shapes may similarly be formed by end forming such that the invention is not intended to be unnecessarily limited to fillet (266) shown in FIG. 12.

Figure 13:
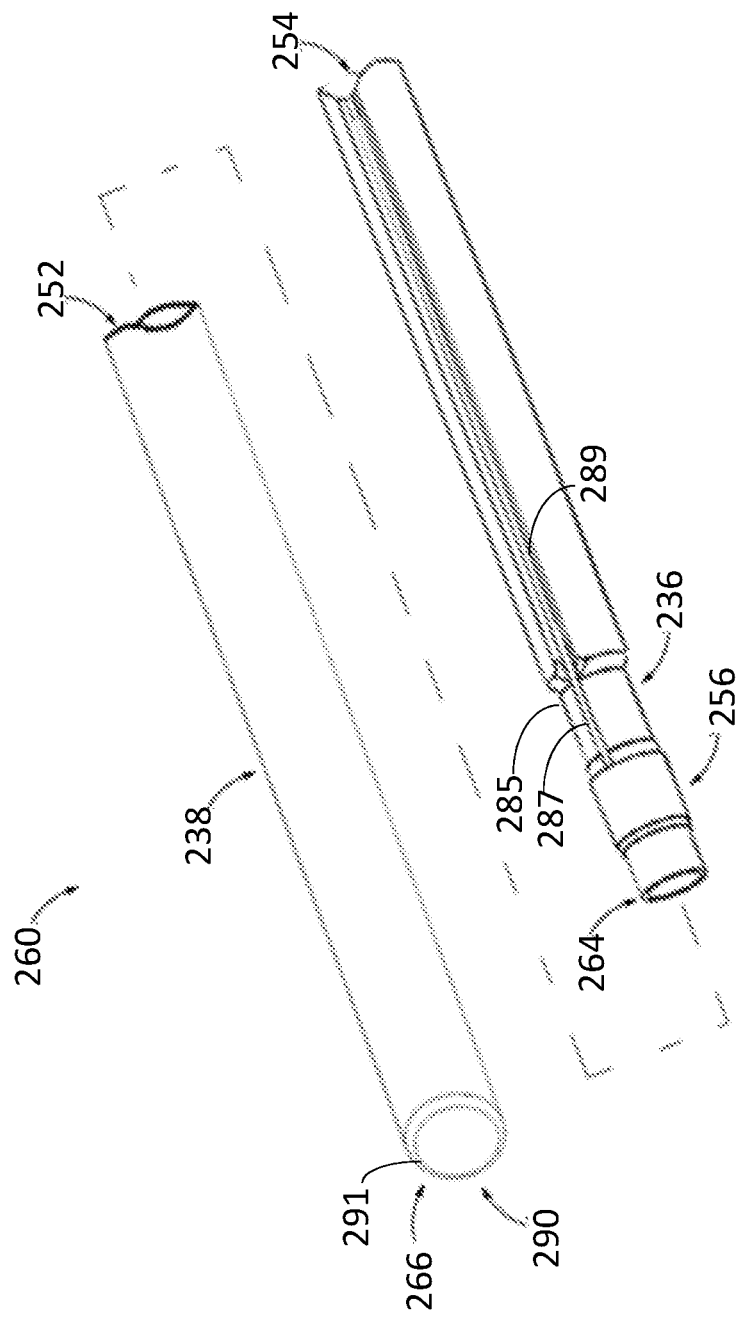
FIG. 13 depicts an enlarged, exploded perspective view of the outer shaft of FIG. 12 receiving the inner shaft of FIG. 8 during assembly.

As shown in FIG. 13, sensor (256) is mounted on necked down end portion (285) of inner shaft (236) and may be tested to determine whether or not sensor (256) is operational so as to be accurately detected by IGS navigation system (10) (see FIG. 1.). If sensor (256) is not operational, sensor (256) is exchanged with another sensor (256) and retested as desired. One or both of outer and inner shafts (238, 236) may also be set aside or returned to production queue for future assembly. After sensor (256) is verified as operational, inner shaft (236) with mounted sensor (256) is inserted into outer tube (238). Inner annular surface (291) engages necked down end portion (285) with tight enough tolerances so the engagement between inner annular surface (291) and inner tube outer diameter (264) may then be welded to form sealed seam (293) (see FIG. 10). Thus, in the present example, no welds are placed on sidewall (252) proximate to sensor (256); and, more particularly, only one weld is placed on distal end 290) away from sensor (256) for inhibiting damage to sensor during manufacturing. Once welded together, inner shaft (236) and outer shaft (238) are assembled as suction shaft assembly (260). Suction shaft assembly (260) may then be attached to grip portion (240) (see FIG. 8) to complete manufacture of surgical suction instrument (200) for use.

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of manufacturing a surgical instrument, wherein the surgical instrument includes a shaft assembly having a first tube, and a second tube, wherein the first tube extends from a proximal first end portion to a distal first end portion, wherein the second tube extends from a proximal second end portion to a distal second end portion and is positioned coaxially within the first tube such that the distal second end portion is positioned adjacent to the distal first end portion, wherein the second tube further includes an opening positioned at or near the distal second end portion and defines a lumen extending from the proximal second end portion to the distal second end portion in communication with the opening, the method comprising: (a) engaging a die against the distal first end portion of the first tube while simultaneously moving the die relative to the distal first end portion of the first tube along a predetermined path to thereby form the distal first end portion with a predetermined shape to thereby manufacture at least a distal portion of the surgical instrument.

Example 2

The method of Example 1, further comprising heating the distal first end portion of the first tube.

Example 3

The method of any one or more of Examples 1 through 2, further comprising rotating the first tube relative to the die.

Example 4

The method of any one or more of Examples 1 through 3, wherein moving the die further includes translating the die relative to the distal first end portion along the predetermined path such that at least a portion of the predetermined path includes a predetermined arcuate path portion.

Example 5

The method of any one or more of Examples 1 through 4, wherein the predetermined shape is a predetermined hemispherical dome shape.

Example 6

The method of any one or more of Examples 1 through 5, further comprising forming a first window opening in the distal first end portion of the first tube, wherein the first window opening is configured to communicate with a second window opening in the distal second end portion of the second tube.

Example 7

The method of any one or more of Examples 1 through 4, wherein the predetermined shape is a coaxial hole extending through the distal first end portion and surrounded by a second radial surface sized to engage a first radial surface of the distal second end portion.

Example 8

The method of any one or more of Examples through 7, wherein the first tube is unitarily formed from the distal first end portion to the proximal first end portion.

Example 9

The method of any one or more of Examples 1 through 8, further comprising securing a position sensor to the first tube or the second tube.

Example 10

The method of Example 9, further comprising testing the position sensor, wherein testing the position sensor includes: (i) measuring a resistivity value of the position sensor, (ii) comparing the measured resistivity value to a threshold resistivity value, and (iii) determining whether or not the position sensor is operable based on the comparison of the measured resistivity value to the threshold resistivity value.

Example 11

The method of any one or more of Examples 1 through 10, further comprising inserting the second tube into the first tube thereby assembling at least a portion of the shaft assembly such that the distal second end portion engages the distal first end portion.

Example 12

The method of Example 11, further comprising welding the first tube to the second tube at the engagement therebetween to define a seam therebetween.

Example 13

The method of Example 12, wherein the shaft assembly has a distal assembly face and the seam is positioned on the distal assembly face.

Example 14

The method of any one or more of Examples 12 through 13, wherein the shaft assembly has only one seam between the first tube and the second tube.

Example 15

The method of any one or more of Examples 11 through 14, further comprising: (i) securing a position sensor to the first tube or the second tube, and (ii) testing the position sensor to determine whether or not the sensor is operational for being detected by the navigation system, wherein testing occurs after inserting the second tube into the first tube and prior to welding the first tube to the second tube.

Example 16

A method of manufacturing a surgical cutting instrument, comprising: (a) engaging a die against a distal first end portion of a first tube, while simultaneously moving the die relative to the distal first end portion along a predetermined path thereby forming a first predetermined hemi-spherical dome shape at the distal first end portion; (b) forming a first window opening in a sidewall of the distal first end portion; and (c) inserting a second tube having a distal second end portion with a second predetermined hemi-spherical dome shape into the first tube such that the first predetermined hemi-spherical dome shape at the distal first end portion at least partially receives the second predetermined hemi-spherical dome shape at the distal second end portion; and (d) longitudinally aligning a second window opening in the second distal end portion with the first window opening in the first distal end portion thereby manufacturing at least a portion of the surgical instrument such that the first window opening is configured to communicate with the second window opening.

Example 17

The method of Example 16, further comprising rotating the first tube relative to the die while simultaneously engaging the die.

Example 18

A method of manufacturing a surgical suction instrument, comprising: (a) engaging a die against a distal first end portion of a first tube while simultaneously moving the die relative to the distal first end portion of the first tube along a predetermined path thereby forming the distal first end portion with a predetermined shape, wherein the predetermined shape is a coaxial hole extending through the distal first end portion and surrounded by an inner radial surface sized to engage an outer radial surface of a second tube; (b) inserting the second tube into the first tube such that the inner radial surface of the distal first end portion engages the outer radial surface of the second tube; (c) positioning a position sensor on a distal second end portion of the second tube; and (d) welding the first tube to the second tube at the engagement therebetween to define a seam and assemble a shaft assembly thereby manufacturing at least a portion of the surgical suction instrument.

Example 19

The method of Example 18, wherein the shaft assembly has only one seam sealing the first tube to the second tube.

Example 20

The method of any one or more of Examples 18 through 19, further comprising rotating the first tube relative to the die about a central longitudinal axis defined by the first tube.

V. MISCELLANEOUS

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of manufacturing a surgical instrument, the surgical instrument including a shaft assembly having a first tube and a second tube, the first tube extending from a proximal first end portion to a distal first end portion along a longitudinal axis, the second tube extending from a proximal second end portion to a distal second end portion and is positioned coaxially within the first tube such that the distal second end portion is positioned adjacent to the distal first end portion, the first tube further including a first window opening positioned at or near the distal first end portion, the second tube further including a second window opening positioned at or near the distal second end portion and defines a lumen extending from the proximal second end portion to the distal second end portion in communication with the second window opening, the method comprising:
 a) rotating the first tube;
 b) engaging a die against the distal first end portion of the first tube while simultaneously rotating the first tube and while simultaneously moving the die relative to the distal first end portion of the first tube along a predetermined path, the predetermined path including a predetermined arcuate path, to thereby form the distal first end portion with a predetermined shape to thereby manufacture at least a distal portion of the surgical instrument;
 c forming the first window opening in the first tube, the first window opening facing radially outward relative to the longitudinal axis; and
 d inserting the second tube into the first tube thereby assembling at least a portion of the shaft assembly such that the first window opening is longitudinally aligned and remains longitudinally aligned with the second window opening.

2. The method of claim 1, further comprising heating the distal first end portion of the first tube.

3. The method of claim 1, further comprising rotating the first tube relative to the die.

4. The method of claim 1, the predetermined shape being a predetermined hemi-spherical dome shape.

5. The method of claim 4, further comprising welding the predetermined hemi-spherical dome shape to seal the predetermined hemi-spherical dome shape.

6. The method of claim 1, the first tube being unitarily formed from the distal first end portion to the proximal first end portion.

7. The method of claim 1, further comprising securing a position sensor to the first tube or the second tube.

8. The method of claim 7, further comprising testing the position sensor, testing the position sensor including:
 i) measuring a resistivity value of the position sensor,
 ii) comparing the measured resistivity value to a threshold resistivity value, and
 iii) determining whether or not the position sensor is operable based on the comparison of the measured resistivity value to the threshold resistivity value.

9. The method of claim 1, the first window opening being formed by machining the opening through a sidewall of the first tube.

10. The method of claim 1, the first window opening being further machined by removing burrs from the first window opening.

11. The method of claim 1, the die being moved in an orbital motion around the distal first end portion.

12. A method of manufacturing a surgical instrument, the surgical instrument including a shaft assembly having a first tube and a second tube, the first tube extending from a proximal first end portion to a distal first end portion along a longitudinal axis, the second tube extending from a proximal second end portion to a distal second end portion and is positioned coaxially within the first tube such that the distal second end portion is positioned adjacent to the distal first end portion, the first tube further including a first window opening positioned at or near the distal first end portion, the second tube further including a second window opening positioned at or near the distal second end portion and defines a lumen extending from the proximal second end portion to the distal second end portion in communication with the second window opening, the method comprising:
   a) engaging a die against the distal first end portion of the first tube while simultaneously moving the die relative to the distal first end portion of the first tube along a predetermined path, to thereby form the distal first end portion having a first hemi-spherical dome shape, to thereby manufacture at least a distal portion of the surgical instrument;
   b) forming the first window opening in the first tube, the first window opening facing radially outward relative to the longitudinal axis; and
   c) inserting the second tube into the first tube thereby assembling at least a portion of the shaft assembly such that the first window opening is longitudinally aligned with, and remains longitudinally aligned with, the second window opening.

13. The method of claim 12, the first window opening including a dull edge, and the second window opening including a cutting edge, the second window opening being rotatable relative to the second window opening to sever tissue between the cutting edge and the dull edge.

14. The method of claim 12, further comprising engaging the die against the distal second end portion of the second tube, while simultaneously rotating the distal second end portion relative to the die and moving the die along the predetermined path, thereby forming a second hemi-spherical dome shape at the distal second end portion.

15. A method of manufacturing a surgical instrument, the surgical instrument including a shaft assembly having a first tube and a second tube, the first tube extending from a proximal first end portion to a distal first end portion along a longitudinal axis, the second tube extending from a proximal second end portion to a distal second end portion and is positioned coaxially within the first tube such that the distal second end portion is positioned adjacent to the distal first end portion, the first tube further including a first window opening positioned at or near the distal first end portion, the second tube further including a second window opening positioned at or near the distal second end portion and defines a lumen extending from the proximal second end portion to the distal second end portion in communication with the second window opening, the method comprising:
   a) engaging a die against the distal first end portion of the empty first tube while simultaneously moving the die relative to the distal first end portion of the empty first tube along a predetermined path, to thereby form the distal first end portion with a hemi-spherical dome shape, to thereby manufacture at least a distal portion of the surgical instrument;
   b) forming the first window opening in the empty first tube, the first window opening facing radially outward relative to the longitudinal axis; and
   c) inserting the empty second tube into the empty first tube, thereby assembling at least a portion of the shaft assembly such that the first window opening is longitudinally aligned with, and remains longitudinally aligned with, the second window opening.

16. The method of claim 15, further comprising:
   a) engaging the die against the distal second end portion of the empty second tube; and
   b) rotating the empty second tube while simultaneously moving the die relative to the distal second end portion of the empty second tube along a second predetermined path, the second predetermined path forming a second hemi-spherical dome shape.

17. The method of claim 16, further comprising forming a second window opening in the empty second tube, the first window opening facing radially outward relative to the longitudinal axis.

18. The method of claim 17, further comprising the first window opening including a dull edge, and the second window opening including a cutting edge, the second window opening being rotatable relative to the second window opening to sever tissue between the cutting edge and the dull edge.

19. The method of claim 18, further comprising rotating the first tube in lathe while simultaneously engaging a die against the distal first end portion of the empty first tube.

20. The method of claim 19, the predetermined path including an arcuate or orbital path.

* * * * *